United States Patent [19]

Shah

[11] 4,340,066
[45] Jul. 20, 1982

[54] MEDICAL DEVICE FOR COLLECTING A BODY SAMPLE

[75] Inventor: Nayan S. Shah, Chesterfield, Mo.

[73] Assignee: Sherwood Medical Industries Inc., St. Louis, Mo.

[21] Appl. No.: 117,677

[22] Filed: Feb. 1, 1980

[51] Int. Cl.³ .............................................. A61B 10/00
[52] U.S. Cl. .................... 128/749; 128/751; 128/754; 128/304
[58] Field of Search ................ 128/751–758, 128/304, 749

[56] References Cited

U.S. PATENT DOCUMENTS

| | | | |
|---|---|---|---|
| 606,052 | 5/1898 | Cook | 128/304 |
| 1,585,934 | 5/1926 | Muir . | |
| 1,867,624 | 7/1932 | Hoffman | 128/754 |
| 3,438,366 | 4/1969 | Kariher et al. . | |
| 3,485,236 | 12/1969 | Frost . | |
| 3,527,203 | 9/1970 | Gravlee . | |
| 3,554,185 | 1/1971 | Kohl . | |
| 3,583,390 | 6/1971 | Jascalevich . | |
| 3,606,878 | 9/1971 | Kellogg, Jr. . | |
| 3,721,244 | 3/1973 | Elmaleh | 128/304 |
| 3,777,743 | 12/1973 | Binard et al. . | |
| 3,931,820 | 1/1976 | Bucalo | 128/757 X |
| 3,945,372 | 3/1976 | Milan et al. | 128/757 |
| 4,055,167 | 10/1977 | Bernstein | 128/758 |
| 4,168,698 | 9/1979 | Ostergard . | |
| 4,282,884 | 8/1981 | Boebel | 128/754 |

FOREIGN PATENT DOCUMENTS

| | | | |
|---|---|---|---|
| 362997 | 11/1922 | Fed. Rep. of Germany . | |
| 2022421 | 12/1979 | United Kingdom | 128/751 |

*Primary Examiner*—Lee S. Cohen
*Assistant Examiner*—J. L. Kruter
*Attorney, Agent, or Firm*—Stanley N. Garber; William R. O'Meara

[57] ABSTRACT

An endometrial sampling device (10) for collecting body material for diagnostic testing includes a handle (12), a generally cylindrical sample collecting member (14, 14a) connected to the handle (12) and having a longitudinal chamber (22, 70), slot (24, 72), and a transverse slot (26) for scraping the walls of the uterus and moving sample material into chamber (22, 70). The handle (12) has a passage (24, 72) connected with the chamber (22, 70) to which a suction force may be applied. A stop member (16) has a slide (36) for gathering collected sample material. The collecting member (14, 14a) is made of a plastic material which can be severed from the handle (12) if desired to convey the sample therein. If desired, the stop member (16) and slide member (36) can be removed from the device (10) after it has gathered the sample.

10 Claims, 7 Drawing Figures

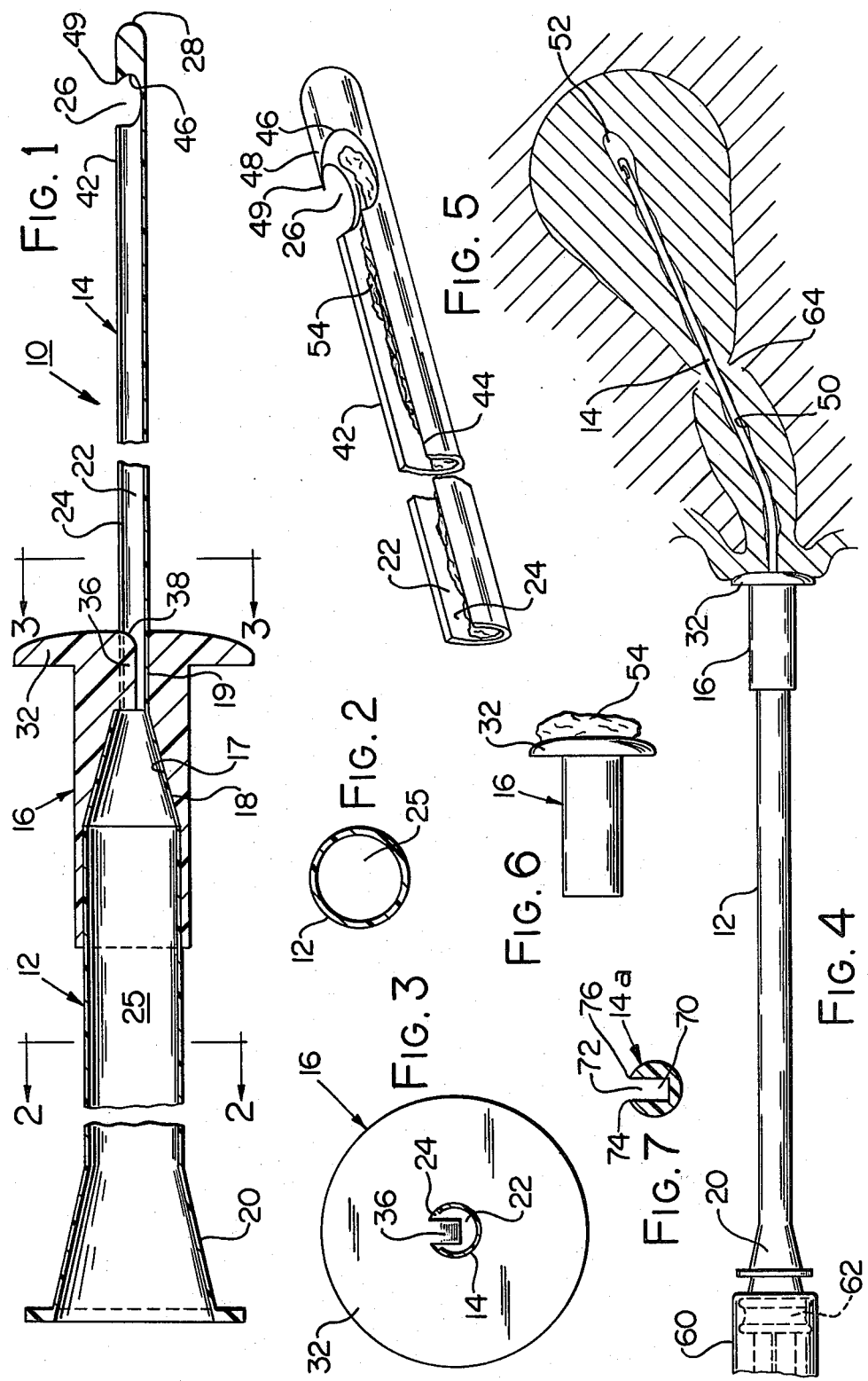

MEDICAL DEVICE FOR COLLECTING A BODY SAMPLE

DESCRIPTION

TECHNICAL FIELD

This invention relates generally to medical sampling devices and more particularly to a medical device and method for collecting sample material from a body cavity for diagnostic purposes.

BACKGROUND ART

Body material sampling devices are used, for example, routinely in determining early uterine cancer. The taking of a cervix smear test, known as the PAP smear test, is generally accomplished by using a generally flat wooden specimen collector which is inserted into the vagina to the entrance to the cervix. The collector with the sample is removed from the patient and the sample subsequently subjected to clinical analysis.

In such smear tests, only sample material in the vagina and near the entrance to the cervix is generally obtained. While smear tests are, of course, important in the early detection of carcinoma of the cervix uteri, it is highly desirable to obtain specimens of body material located higher up in the uterus for a more complete examination. It is especially desirable to obtain specimens of material such as tissue scrapings, cells and fluid from the endometrium for the early detection of endometrial cancer.

Some sampling devices and methods have been proposed for collecting specimens from the uterine cavity or endometrial canal but have not been entirely satisfactory for one reason or another. It has been proposed to use a catheter for introducing a liquid into the uterus and then to withdraw the liquid and separate the sample material from the liquid for purposes of analysis. This method has the disadvantage that it runs the risk of causing abnormal cells to enter other passages, such as the fallopian tubes. In U.S. Pat. No. 3,527,203, a method is disclosed that includes irrigating the uterus with a liquid by means of a catheter and employing suction to the catheter to remove the liquid before it can move cells into the fallopian tubes. However, even if such a method is successful in preventing the spread of abnormal cells to other passages of the body, such a method requires the additional step of removing the sample from the liquid, as well as providing a sample that is not in its natural state.

In U.S. Pat. No. 3,777,743, a sleeve is inserted into the cervix and a suction tube having a section with a plurality of holes, is moved from the sleeve into the uterus. Suction applied to the proximal end of the tube assists movement of endometrial material into the interior of the tube through the holes. This method has the disadvantage that only relatively small amounts of sample material are usually obtained. Also, some material is left in the uterus because of the withdrawal of the suction tube back into the sleeve.

In U.S. Pat. No. 3,438,366, a sleeve is inserted into the cervix and a rod with a piston slideable in the sleeve and provided with a probe is moved such that the probe enters the uterus. A scraping edge at the end of the probe scrapes the endometrial material, and suction aids in drawing the material into the sleeve. This arrangement only permits longitudinal scraping of the endometrial and a limited amount of material is obtained because withdrawal of the rod into the sleeve tends to cause some scraped material to remain in the uterus.

In U.S. Pat. No. 3,945,372, a spiral section of a rod is inserted into the uterus and rotated in a specific direction to scrap and carry sample material. The material moves into the spiral section and when removed by rotation in the same specific direction carries with it the sample material. After removal of the spiral section from the patient, it is passed through a separate member having a slot which member collects the material from the spiral section for test purposes. A disadvantage of this device is that if an error is made in the direction of rotation of the spiral section, the spiral section will pick up little material. If the spiral rotation is in a correct direction during sample collection, improper rotation or rotation in the opposite direction upon removal will cause some of the material to move from the spiral section and remain within the patient.

BRIEF SUMMARY OF THE INVENTION

In accordance with one aspect of the present invention, one or more of the above mentioned problems or disadvantages are overcome.

According to one aspect of the present invention, a sample collection device for insertion into a body cavity for collecting a sample of material from the cavity has a hollow portion with an opening having opposed substantially straight side edges for removing sample material into the hollow portion in response to rotation of the collecting member. In accordance with another aspect of the present invention, a transverse slot is provided in the collection device which permits scraping of the cavity wall by longitudinal movement of the device. The hollow portion and the slot retain sample material during withdrawal. In another aspect of the invention, a slideable gathering member normally on the device is moved longitudinally along the hollow portion to gather the collected sample material.

In still another aspect, a slide member is moved along the hollow portion after the device is removed from the patient to gather the collected sample material.

BRIEF DESCRIPTION OF THE DRAWING

FIG. 1 is a side elevational enlarged view in cross-section of a medical sampling device in accordance with a preferred embodiment of the present invention;

FIG. 2 is a cross-sectional view taken along the line 2—2 of FIG. 1;

FIG. 3 is a slightly enlarged cross-sectional view taken along the line 3—3 of FIG. 1;

FIG. 4 is a plan view of the device of FIG. 1 shown in use;

FIG. 5 is a perspective view of the sample collection portion of the device of FIG. 1 after sample material has been collected therein and the collection portion removed from the device;

FIG. 6 is a side elevational view of the sample gathering and stop member of FIG. 1 illustrating a method of gathering collected material from the device of FIG. 1; and FIG. 7 is an enlarged cross-sectional view of a modified form of a body collecting member.

DETAILED DESCRIPTION OF THE INVENTION

Referring now to the drawing, and particularly to FIG. 1, a medical sampling or specimen collection device 10, illustrated as an endometrial collection device, is shown including a handle 12, a sample collecting portion or member 14 connected integrally to the handle 12, and a movable stop member 16 having an opening 17 with walls connected in tight frictional surrounding relation with the distal end portion 18 of the handle 12, and also in surrounding relation with a proximal portion 19 of the collection member 14. The handle 12 is provided with a luer slip connector 20 at the proximal end which is adapted for fluid tight connection with a luer connector of a syringe or other device capable of providing a negative pressure, as will be discussed hereafter.

The sample collection member 14 is shown as a hollow member having a sample collection or storage chamber 22 and a longitudinal slot or opening 24 extending through the sidewall of the member 14 to the chamber 22. The chamber 22 is in fluid communication with a lumen or fluid passage 25 extending longitudinally through the handle 12, as seen also in FIG. 2. Collection member 14 is also provided with a slot or groove 26 which extends transversely of the longitudinal axis of the member 14 and the slot 24, and is disposed adjacent the distal end, indicated at 28, of member 14. The sample collection member 14 handle 12, and luer connector 20 are preferably formed integrally with each other, such as by molding a suitable plastic material, for example, polyethylene, polyvinyl chloride or other thermoplastic material.

The stop member 16 is provided with a radial flange 32 and an inwardly extending sample material gathering slide or scraper 36, shown also in FIG. 3. Slide 36 extends through slot 24 and into chamber 22 of member 14 and has a proximally inclined or rounded leading edge 38 (FIG. 1). While the stop member 16 is normally secured in tight frictional engagement with the handle 12 for movement with the handle, it can be moved relative to the handle or removed from it. For example, by hand-grasping the handle 12 and, with the thumb, applying a force to the flange 32 in a distal direction, the stop member 16 and slide 36 can be released from the handle and moved distally along the collecting member 14 for gathering sample material, as will be discussed hereafter.

The collecting member 14 is preferably molded in the form of a tube having a constant wall thickness with the wall extending circumferentially at least 180°, and preferably about 270° as shown in the drawing (FIGS. 3 and 5). The slot 24 provides opposed slot edges 42 and 44 spaced circumferentially less than 180° and may be about 90° apart. These edges 42 and 44 respectively provide scraping edges when the member 14 is rotated in opposite directions. The transverse slot 26 is shown intersecting the slot 24 and chamber 22 and it provides scraping edges 46 forming a hook 48 having a point 49 which is pointed in a proximal direction. Edges 46 curve distally from point 49 and then proximally, the edges and point scraping the uterine lining for movement of the collecting member 14 in an outward or proximal direction to collect sampling material therein. The point 49 is in the outer surface of end portion 28 and may be radially inwardly of the slot 24 if desired.

In use, the handle 12 is grasped and the sample collecting member 14 is inserted into the cervical canal, indicated at 50 in FIG. 4, and then into the endometrial cavity 52, until the distal side of stop member 16 engages the cervix, the position of device 10 in FIG. 4. The handle 12 can then be rotated in either direction to effect rotation of the sample collecting member 14 and scrape the endometrium and move endometrial sampling material, tissue, cells and liquid through slot 24 and into the collection chamber 22. For example, when the handle is rotated in the clockwise direction as viewed in FIGS. 3 and 4, the edge 42 of slot 24 will scrape the internal uterine lining including the cervical canal and the endometrial cavity causing sampling material to move into the longitudinal slot 24 and chamber 22. If the handle 12 is rotated in the counterclockwise direction, the leading edge 44 of the collecting member 14 will scrape material from the uterine lining, including the cervix and endometrial cavity, and move it into the slot 24 and chamber 22. When the device 10 is moved longitudinally outwardly or proximally from the position shown in FIG. 4, the edge 46 of transverse slot 26 will scrape the internal uterine lining and including the endometrium and collect material in the slot 26 during this longitudinal movement of the device 10 from the uterus. Upon removal of the device 10 from the patient, the cervical and endometrial sampling material will be within the collection or storage chamber 22. It will be apparent that during withdrawal of the device 10 from the patient, the chamber walls will prevent collected material from being scraped from the device. Thus, a relatively large amount of sample material is obtained.

In some cases, it is desirable to cut off the sample-filled collecting member 14 such as at a point adjacent the distal side of the stop member 16. FIG. 5 shows the plastic collecting member 14 cut off and filled with cervix and endometrial sampling material which is indicated at 54. The cut off part shown in FIG. 5 may be placed in a container for shipment to a diagnostic laboratory where the material may be scraped from member 14 for clinical testing.

Alternatively, instead of cutting off the sample collecting member 14 from the rest of device 10 after collecting a sample, the slide 36 of stop member 16 may be used to gather and remove the collected sample material 54. In such case, the member 16 is forced from the distal end 18 of the handle 12, for example, by applying thumb pressure in a distal direction to the flange 32 as previously mentioned. When loose, the stop 16 is moved distally toward the distal end 28 of the collecting member 14. As it moves longitudinally along slot 24 and the chamber 22, the slide member 36 pushes the sampling material 54 ahead of it causing the material to gather as it moves distally. The stop member 16 may be moved completely off of the distal end of the collecting member 14. For example, as member 16 moves to the end portion 28, the sloping or rounded end 38 of the sample gathering slide member 36 will engage the edge 46 of transverse slot 26 and slide over it. For example, the rounded end of member 36 can cause the end 28 to bend downwardly, as viewed in FIG. 1, so that the member 16 will readily move off of the collecting member 14. In FIG. 6, the stop member 16 is shown removed from the device 12 and carrying the gathered cervical and endometrial sample 54 on the distal side of it. The material 54 in FIG. 6 may be transferred directly to smear slides or the sample with the member 16 may be placed in a container for shipment to a laboratory. If desired, the slide 36 can be used to gather the sample material at the slot 26 where the material can be readily removed without removing the member 16 from member 14.

Instead of cutting off the collecting member 14, as shown in FIG. 5, or gathering the material onto the stop member 16 and removing the stop member from the device 10, as indicated in FIG. 6, the material in storage chamber 22 and any on the outer surface of the member 14 after it is removed from the patient, may be removed by any suitable means and placed directly onto slides or the like for test purposes without first gathering it together. One advantage of removing the material without gathering it together is that tests may be run on different portions of the sample material with the tests providing an indication of the condition of the uterus at corresponding different locations along the uterus.

Since the viscosity or consistency of the endometrial sampling material may vary, it may be desirable to apply a vacuum or suction force to the chamber 22 of collecting member 14 to cause the endometrium to move closely to the edges 42 and 44 so that material can be readily scrapped from the walls and moved through slot 24 and into the collection chamber. Referring again to FIG. 4, a syringe 60 is shown connected to the connector 20 for applying a suction force to the passage 25 and chamber 22 while the collecting member 14 is within the uterus as shown. In such a case, the syringe piston, shown in phantom at 62, is moved proximally to cause a negative pressure within the chamber 22 tending to draw the walls of the uterus toward the member 14.

The endometrial sampler 10 is constructed to enter the cervix and pass into the uterine cavity or endometrial portion of the uterus without damaging the lining of the uterus. The outer diameter of the sample collecting member 14 is preferably about 2.5 millimeters and should be relatively flexible plastic so that it readily assumes the anatomical nature or curvature of the cervical canal and endometrial canal or cavity. It should however be stiff or hard enough to rotate in response to the rotation of handle 12 and without collapsing the collection chamber 22 or closing slot 24. In some cases, where desired, the collecting member 14 may be given a preset curvature, such as in the mold, that will facilitate the insertion of it into the uterus. Based on the average size adult uterus, slot 24 and chamber 22 generally should be at least 2.5 centimeters in length in order to obtain a desirable amount of endometrial material, and preferably it extends from a location adjacent the distal tip 28 or slot 26 of member 14 to a location adjacent the stop 16 as is shown in the drawing. The actual length of the member 14 is preferably about 7 or 8 centimeters and the slot chamber about 6 or 7 centimeters in length. Where it is desired to obtain only endometrial material, the member 14 need not be slotted proximally beyond the distal end 64 (FIG. 4) of the cervix when device 10 is in place as in FIG. 4. It is preferred that the slot and collection chamber extend continuously from about the distal end 28 of member 14 or slot 26 to at least the distal end 64 of the cervix.

The chamber 22 provides a cervical and endometrial sample storage container which allows the withdrawal of the sampling device from the patient while retaining substantially all of the material collected in the chamber during the scraping portion of the sampling steps. Large as well as small sample portions, as well as liquids and semiliquids, are readily moved into the longitudinal slot and chamber and remain in their respective locations along the slot after removal of the device from the patient. Thus, a relatively large material sampling can be obtained during a single sampling operation. This insures that the sampling operation can be accomplished in one sampling operation rather than requiring repeated sampling with a considerable amount of discomfort to the patient.

In FIG. 7, a modified form of a sample collecting member 14a is shown having a sample collection chamber 70, and a longitudinal slot 72 connecting chamber 70 to the exterior of the member. Slot 72 provides a pair of opposed straight slot side edges 74 and 76. The edges 74 and 76 provide scraping edges for moving endocervical and endometrial sampling material or other body specimen materials through the slot 72 and into the collection chamber 70 when rotated respectively in opposite directions in the uterus.

The stop members 16 may be made of a suitable plastic, for example, the same plastic used making handle and collection member. In assembling the device 10, the stop member 16 can be forced over the distal end 28 of the flexible plastic member 14 and the slide 36 moved into the distal end slot 26 and then slot 24.

It will now be apparent that there are several effective methods of obtaining a desired body cavity sample. Also, in addition to the use of the device 10 as an endometrial sampling device, it may also be used in other body cavity sampling operations. For example, it is possible to use it to obtain a sample from the alimentary canal to test for rectal cancer or the device 10 could be used for obtaining a sample from the urethra to test for gonorrhea.

The member 14 or 14a is preferably generally cylindrical or circular in cross-sections except in the areas of the longitudinal and transverse slots, for easy insertion of, rotation and withdrawal.

Preferably, the scraping edges 42 and 44 are straight and parallel with the longitudinal axis of the member 14, and extend from a transverse slot 26 or a point near the distal end 28 to a point near the material gathering slide 36 as shown. This construction permits a relatively large amount of sample material to be obtained from a relatively large area of the uterus and allows use of the convenient sample gathering member 36. Also, with straight edges 42 and 44 the device 10 can be rotated in either direction while in the uterus or during withdrawal substantially without loss of sample material previously collected in chamber 22.

While the transverse slot 26 is shown connected with the longitudinal chamber 22, the chamber could stop, if desired, short of the slot. Also, transverse slot 26 could be formed at a location circumferentially offset from the chamber 22 and more than one transverse slot and/or hook could be used if desired. By forming the hook 48, so that it substantially does not protrude radially outwardly beyond the average outer diameter of the member 14 or end 28, removal or insertion of the member 14 will not damage the walls of the body cavities under normal usage of the device 10.

As various changes could be made in the above construction without departing from the scope of the invention, it is intended that all matter contained in the above description or shown in the accompanying drawing shall be interpreted as illustrative and not in a limiting sense.

I claim:

1. A medical specimen collection device (10) comprising a handle (12) and an elongate sample collecting member (14, 14a) connected to said handle (12) for insertion into a body cavity for collecting sample material therefrom, at least a portion of said member (14, 14a) being hollow to provide a generally longitudinal chamber (22, 70) therein for receiving sample material and having a generally longitudinal slot (24, 72) through the sidewall thereof to said chamber (22, 70), said slot (24, 72) having opposed side edges extending generally parallel to the longitudinal axis of said member for scraping sample material from a body cavity through said slot (24, 72) and into said chamber (22, 70) in response to rotation of said member (14, 14a) when in a body cavity, and sample gathering means (36) mounted adjacent the handle (12) of the device for movement relative to said collecting member (14, 14a) and extending through said longitudinal slot (24, 72) and into said chamber (22, 70), said gathering means (36) being distally longitudinally slideable along said slot and chamber from an initial proximal position to a relatively distal position after said member is removed from the body cavity to move sample material collected in said chamber (22, 70) in a distal direction to gather the same.

2. The device of claim 1 further including a radial stop member (16) engageable with the body of a patient at the entrance to the body cavity to stop inward movement of said collecting member, said longitudinal slot (24, 72) and chamber (22, 70) substantially extending proximally from a point near the distal end of said collecting member (14, 14a) to a point near said stop member (16).

3. The device of claim 1 wherein said chamber (22, 70) and slot (24, 72) are long enough to extend through the cervical canal when the device (10) is inserted in the endometrium of a patient to effect scraping of the cervical canal walls and move cervical material therefrom into said chamber (22, 70), said gathering means is disposed exteriorly to the cervical canal of the patient when said member extends into the endometrium of the patient.

4. A medical specimen collection device (10) comprising a handle (12) and an elongate sample collecting member (14, 14a) connected to said handle (12) for insertion into a body cavity for collecting sample material therefrom, at least a portion of said member (14, 14a) being hollow to provide a chamber (22, 70) having a longitudinal length substantially greater than its width, and a slot (24, 72) in the side wall of said collecting member having opposed side edges extending parallel to the longitudinal axis of said member for scraping sample material through said slot (24, 72) and into said chamber (22, 70) in response to rotation of said member (14, 14a) when in a body cavity, said chamber (22, 70) and said slot (24, 72) being at least 2.5 centimeters in length, and a radial stop member (16) engageable with the body of a patient at the entrance to the body cavity to stop inward movement of said collecting member and being slideable longitudinally along said collecting member (14, 14a), said stop member (16) having a sample material pusher member (36) extending into said longitudinal slot (24, 72) and chamber (22, 70) and movable distally with said stop member (16) from an initial position to a position adjacent the distal end (28) of said collecting member (14, 14a) to gather sample material collected in said chamber (22, 70).

5. The device of claim 4 wherein said handle (12) has a longitudinal passage (25) connected in fluid communication with said chamber (22, 70) and means (20) for connecting a source (60) of negative pressure to said passage (25) for applying a negative pressure at said chamber (22, 70) when said collecting member (14, 14a) is in a body cavity for facilitating the collection of body material in said chamber (22, 70).

6. The device of claim 4 wherein said edges (42, 44, 74, 76) are substantially less than 180° apart, and said collection member is cylindrical and the walls thereof are of substantially constant thickness.

7. A medical specimen collection device (10) comprising a handle (12) and an elongate sample collecting member (14, 14a) connected to said handle (12) for insertion into a body cavity for collecting sample material therefrom, at least a portion of said member (14, 14a) being hollow to provide a chamber (22, 70) therein for receiving sample material and having a longitudinal extending slot (24, 72) extending through the sidewall of said member to said chamber (22, 70) and having a longitudinal length substantially greater than its width, said slot (24, 72) having opposed side edges extending parallel to the longitudinal axis of said member for scraping sample material through said slot (24, 72) and into said chamber (22, 70) in response to rotation of said member (14, 14a) when in a body cavity, said collecting member (14, 14a) having at least one transverse slot (26) having an edge (46) for moving sample material into said transverse slot (26) in response to longitudinal movement of said collecting member (14, 14a), said transverse slot (26) intersecting said longitudinal slot (24, 72) adjacent to the distal end (28) of said collecting member (14, 14a), and a radial stop member (16) engageable with the body of a patient at the entrance to the body cavity to stop inward movement of said collecting member and being slideable longitudinally along said collecting member (14, 14a), said stop member (16) having a sample material pusher (36) extending into said longitudinal slot (24, 72) and chamber (22, 70) and movable distally with said stop member (16) from an initial position to a position adjacent the distal end (28) of said collecting member (14, 14a) to gather sample material collected in said chamber (22, 70).

8. An endometrial sampling device (10) comprising an elongate handle (12), a generally cylindrical sample collecting member (14, 14a) connected to said handle (12) for insertion through the cervical canal and into the endometrial cavity of a patient for collecting endometrial sample material therefrom, said collecting member (14, 14a) having a longitudinally extending chamber (22, 70) therein, a longitudinally extending slot (24, 72) extending through the sidewall of said collecting member (14, 14a) to said chamber (22, 70) and having spaced, opposed straight edges (42, 44, 74, 76) at the periphery thereof for scraping sample material including endometrial material into said chamber (22, 70) in response to rotation of said collecting member (14, 14a) in either direction of rotation, said edges (42, 44, 74, 76) being at least 2.5 centimeters in length, a stop member (16) engageable with the proximal end of the cervix to limit movement of said collecting member (14, 14a) into the uterus, said chamber (22, 70) and said longitudinal slot (24, 72) extending continuously substantially from said stop member (16) at least to a point near the distal end of said collecting member (14, 14a), and a slide member mounted adjacent to the handle (12) (36) extending through said longitudinal slot (24, 72) and into said chamber (22, 70), said slide member (36) being slideable distally along said slot (24, 72) for gathering sample material collected in said chamber (22, 70), said slide member being connected to said stop member (16) and said stop member being movable to effect movement of said slide member (36).

9. The device of claim 8 wherein said slide member (36) is movable over the distal end (28) of said collecting member (14, 14a) to carry collected sampling material with it.

10. The device of claim 9 or 8 wherein said edges (42, 44, 74, 76) are substantially parallel to the longitudinal axis of said member (14, 14a).

* * * * *